United States Patent
Wandrey et al.

(10) Patent No.: US 7,022,503 B2
(45) Date of Patent: Apr. 4, 2006

(54) PROCESS FOR THE STEREOSELECTIVE PREPARATION OF FUNCTIONALIZED VICINAL DIOLS

(75) Inventors: Christian Wandrey, Jülich (DE); Murillo De Oliveira Villela Filho, Cotia-SP (BR); Andreas Liese, Jülich (DE); Jan A. M. De Bont, AK Wageningen (NL); Jan C. Verdoes, KR Wageningen (NL); Carel A. G. M. Weijers, DW Nijmegen (NL); J. Hans Visser, NJ Nijmegen (NL); Claus Dreisbach, Leichlingen (DE)

(73) Assignees: Bayer Aktiengesellschaft, Leverkusen (DE); Forschungszentrum Juelich GmbH, Juelich (DE)

( * ) Notice: Subject to any disclaimer, the term of this patent is extended or adjusted under 35 U.S.C. 154(b) by 332 days.

(21) Appl. No.: 10/238,308

(22) Filed: Sep. 9, 2002

(65) Prior Publication Data

US 2003/0134401 A1    Jul. 17, 2003

(30) Foreign Application Priority Data

Sep. 11, 2001  (EP) ................................ 01120796

(51) Int. Cl.
*C12P 7/44* (2006.01)
*C12P 7/46* (2006.01)
*C12N 9/16* (2006.01)

(52) U.S. Cl. ............... 435/142; 435/145; 435/195; 435/196; 435/254.2

(58) Field of Classification Search .............. 435/142, 435/145, 195, 196, 254.2
See application file for complete search history.

(56) References Cited

U.S. PATENT DOCUMENTS

| | | | |
|---|---|---|---|
| 3,976,546 A * | 8/1976 | Smith et al. | 435/48 |
| 4,379,920 A * | 4/1983 | Brown et al. | 540/221 |
| 4,533,632 A * | 8/1985 | Smith et al. | 435/47 |
| 5,726,055 A * | 3/1998 | Hindley et al. | 435/280 |
| 6,379,938 B1 * | 4/2002 | Dauvrin et al. | 435/158 |

OTHER PUBLICATIONS

Weijers, Carel A. G. M. et al;"Epoxide hydrolases from yeasts and other sources: versatile tools in biocatalysis" retrieved from STN Database accession No. 130:293060, XP002189633 *abstract* & J. Mol. Catal. B: Enzym. (1999), 6(3), 199-214.

Krenn, Wolfram et al. "Bacterial epoxide hydrolases of opposite enantiopreference" retrieved from STN Database accession No. 131:333942, XP002189634 *abstract* & Biotechnol. Lett. (1999), 21(8), 687-690.

Greene J. F. et al: "Metabolism of monoepoxides of methyl linoleate: Bioactivation and detoxification." Archives of Biochemistry and Biophysics, vol. 376, No. 2, 2000, pp. 420-432, XP002189628.

Blee E. and Schuber F.: "Regio- and Enantioselectivity of Soybean Fatty Acid Epoxide Hydrolase." J. Biol. Chem. vol. 267, No. 17, 1992, pp. 11881-1187, XP002189629, see especially p. 11886 *the whole document*.

Visser, H. et al: "Cloning and characterization of an epoxide hydrolase-encoding gene from *Rhodotorula glutinis*" retrieved from STN, Database accession No. 133:234299, XP002189630 *abstract* & Appl. Microbiol. Biotechnol. (2000), 53(4), 415-419.

Weijers, Carel A. G. M.: "Enantioselective hydrolysis of aryl, alicyclic and allphatic epoxides by *Rhodotorula glutinis*" retrieved from STN Database accession No. 126: 263661, XP002189631 *abstract* & Tetrahedron: Asymmetry (1997), 8(4), 639-647.

Botes, A. L. et al: "Biocatalytic resolution of 1,2-epoxyoctane using resting cells of different yeast strains with novel epoxide hydrolase activities" retrieved from STN Database accession No. 129:25538, XP002189632 *abstract* & Biotachnol. Lett. (1998), 20(4), 421-426.

* cited by examiner

*Primary Examiner*—Herbert J. Lilling
(74) *Attorney, Agent, or Firm*—Jennifer R. Seng

(57) ABSTRACT

The present invention relates to a process for the kinetic resolution of racemic functionalized epoxides in the presence of microorganisms, crude or pure preparations thereof comprising a polypeptide having epoxide hydrolase activity. Preferred microorganisms are yeasts and bacteria which may also be recombinant.

21 Claims, No Drawings

PROCESS FOR THE STEREOSELECTIVE PREPARATION OF FUNCTIONALIZED VICINAL DIOLS

BACKGROUND OF THE INVENTION

1. Field of the Invention

The present invention relates to a process for the stereoselective preparation of vicinal diols by kinetic resolution of functionalized oxiranes using epoxide hydrolases, and an improved process for the preparation of recombinant epoxide hydrolases.

2. Brief Description of the Prior Art

Enantiopure epoxides and the vicinal diols derived therefrom, especially those with further functional groups like carboxylic groups and derivatives thereof are valuable products with biological activity or serve as versatile chiral building blocks for more complex biologically active compounds. Therefore, a great interest exists in the development of methods for the synthesis of such compounds.

P. Hutin and M. Larcheveque (Synthesis 2000, No. 2, p. 220–222) developed a three step synthesis for the preparation of protected 2,3-dihydroxycarbonitriles as a mixture of syn and anti-isomers. This mixture could further be resolved by chromatography. Despite the fact that the enantiomeric purity is satisfying, the procedure has several disadvantages like the need of chiral precursors, an expensive reductant (diisobutyl-aluminiumhydride, DIBALH) and the restriction to carbonitriles as products. Thus it is not suitable for an industrial scale production. Therefore there is still the need for a technically feasible process for the stereoselective preparation of functionalized vicinal diols on an industrial scale.

It is known that some epoxide hydrolases of mammals, plants, insects, bacteria and yeasts are capable of kinetic resolution of racemic epoxides.

Kinetic resolution means that, for example, in an racemic mixture one enantiomer is hydrolized significantly faster than the other, which leads to the formation of enantiomerically enriched vicinal diols and epoxides (the non-converted starting enantiomer) (see also Weijers et al., Appl. Microb. Biotechnol., 1995, 42, 775). But up till now, only unfunctionalized vicinal diols could be obtained via this biochemical route (see for example R.-N. Patel, Stereoselective "synthesis using microbial epoxide hydrolases" in W. Kroutil, K. Faber "Stereoselective biocatalysis", p. 205–237, Marcel Dekker, New York, 2000.

SUMMARY OF THE INVENTION

Surprisingly, a process has now been found for the stereoselective preparation of 2,3-dihydroxycarboxylic acids and derivatives thereof, which is characterized in that 2,3-epoxycarboxylic acids or derivatives thereof are hydrolysed in the presence of a polypeptide having epoxide hydrolase activity.

In a preferred embodiment of the invention, epoxides of the general formula (I)

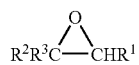
(I)

wherein independently of each other
R$^1$ represents a carboxylic group or a derivative thereof R$^2$ represents hydrogen, straight-chain or branched, cyclic or acyclic C$_1$–C$_{12}$-alkyl, unsubstituted or substituted aryl and R$^3$ represents hydrogen or straight-chain C$_1$–C$_{12}$-alkyl or R$^2$R$^3$C as whole represents a carbocycle or a heterocycle, are hydrolysed to vicinal diols of the general formula (II)

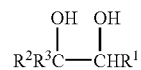
(II)

wherein R$^1$, R$^2$ and R$^3$ have the same meaning as mentioned above in the presence of a polypeptide having epoxide hydrolase activity and which is derived from a microorganism.

Carboxylic groups or derivatives thereof for example include residues like cyano and those of the general formula (III)

(III)

in which
R$^4$ represents OR$^5$, OM, N(R$^5$)$_2$, or SR$^5$,
wherein
M represents an alkali metal ion or a half equivalent of an earth alkali metal ion or ammonium or N(R$^5$)$_4{}^+$
and
wherein
R$^5$ represents hydrogen, straight-chain or branched, cyclic or acyclic C$_1$–C$_{12}$-alkyl, C$_6$–C$_{12}$-aryl or C$_7$–C$_{13}$-arylalkyl or N(R$^5$)$_2$ as whole represents a heterocycle.

Substituted straight-chain or branched, cyclic or acyclic C$_1$–C$_{12}$-alkyl-residues also include alkyl substituents which are further substituted by halogen, C$_1$–C$_4$-alkoxy, C$_1$–C$_4$-alkylthio, substituted or unsubstituted aryloxy, substituted or unsubstituted aryl, cyano or carboxylic groups or derivatives thereof according to the general formula (III).

Substituted or unsubstituted aryl or aryloxy substituents in all contexts mentioned above are for example carbocyclic aryl or aryloxy substituents having 6 to 12 ring carbon atoms or heteroaryl or heteroaryloxy substituents having 5 to 12 ring carbon atoms in which in every cycle one, two or three of these but at least one in the whole substituent are replaced by a hetero atom selected from the group oxygen, nitrogen and sulfur. Moreover, every carbocyclic aryl or aryloxy substituent or heteroaryl or heteroaryloxy substituent may carry up to three further substituents per cycle independently and exemplaryly selected from the group consisting of iodo, bromo, chloro, fluoro, nitro, cyano, C$_1$–C$_6$-alkyl, C$_1$–C$_6$-fluoroalkyl, C$_1$–C$_6$-alkoxy, amino, di(C$_1$–C$_4$-alkyl)amino, amino-(C$_1$–C$_4$)-acyl, (C$_1$–C$_4$-alkyl)-amino-, carboxyl or derivatives thereof according to the general formula (III), or SO$_3$M with M being an alkali metal ion or a half equivalent of an earth alkali metal ion or ammonium or organic ammonium.

Fluoroalkyl residues are alkyl residues in which at least one hydrogen atom is substituted by fluorine.

Preferred compounds as substrate for kinetic resolution are those of the general formula (I), wherein independently of each other
R¹ represents cyano or substituents of the general formula (III)

in which
R⁴ represents methoxy, ethoxy, isopropoxy, n-propoxy, n-butoxy, sec.-butoxy, tert.-butoxy, benzyloxy, 2-benzyloxy-ethoxy, OH, OLi, ONa, OK, ONH₄, NH₂, methylamino, ethylamino, dimethylamino, diethylamino, pyrrolidino, methylthio, ethylthio,
and
R² represents hydrogen, methyl, ethyl, n-propyl, iso-propyl, n-butyl, sec.-butyl, tert.-butyl, n-pentyl, n-hexyl, cyclohexyl, n-heptyl, n-octyl, benzyloxy, 2-benzyloxy-ethoxy, phenyl, p-tolyl, p-anisyl and
R³ represents hydrogen, methyl, ethyl, n-propyl, n-butyl, n-pentyl, n-hexyl, n-heptyl, n-octyl or
R²R³C as whole represents a five-, six- or seven-membered carbocycle.

Particularly preferred compounds as substrate for kinetic resolution are those of the general formula (I), wherein independently of each other
R¹ represents cyano and
R² represents methyl, ethyl, n-propyl, iso-propyl, n-butyl, sec.-butyl, tert.-butyl, n-pentyl, n-hexyl, cyclohexyl, n-heptyl, n-octyl, phenyl and
R³ represents methyl and
1-oxa-spiro[2,5]octane-2-carbonitrile.

Most particularly preferred compounds as substrate for kinetic resolution are 2-cyano-3,3-dimethoxyoxirane and 1-oxa-spiro[2,5]octane-2-carbonitrile.

All substrate epoxides are either commercially available or can be synthesized according to the method described by Jonczyk et al., Tetrahedron Letters, 23, 1972, p. 2395–2396.

Stereoselective in this context means that one stereoisomer, i.e., enantiomer or a pair of diastereomers is produced in an excess compared to the other enantiomer or pair of diastereomers.

The presence of a polypeptide having epoxide hydrolase activity (in the following referred to as Eph) derived from a microorganism in this context means that the process is carried out for example in the presence of whole cells or cultures of a microorganism or crude or pure preparations thereof comprising said polypeptide. These preparations may be for example crude cell extracts or purified cell extracts, or if Eph is secreted by the microorganism into the culture medium, crude or purified preparations of the culture medium.

Furthermore Eph may also be used in an immobilized form. Processes for immobilisation are per se known to one skilled in the art.

The procedure for isolation and purification of an epoxide hydrolase from *Rhodotorula glutinis* was already described for example in Kronenburg et al., Biotechnol. Letters, 1999, vol. 21, 519–524.

Suitable microorganisms are for example yeasts and bacteria which either naturally produce an Eph or serve as a host cell comprising a recombinant DNA molecule having a nucleotide sequence encoding at least a functional part of an Eph.

Preferably the Eph is derived from a microorganism belonging to the basidiomycetous yeast genera *Rhodotorula*, *Rhodosporidium* or Trichosporon or from a host cell comprising a recombinant DNA molecule having a nucleotide sequence encoding at least a functional part of an Eph, said nucleotide sequence being obtained from above mentioned basidiomycetous yeast genera.

Particularly preferred is the use of an Eph is which is derived from a microorganism belonging to the basidiomycetous yeast genera *Rhodotorula* and *Rhodosporidium* or or from a host cell comprising a recombinant DNA molecule having a nucleotide sequence encoding at least a functional part of an Eph, said nucleotide sequence being obtained from the genera *Rhodotorula* or *Rhodosporidium*.

More particularly preferred is the use of an Eph is which is derived from *Rhodotorula glutinis* strain CBS 8761 or *Rhodotorula araucariae* strain CBS 6031 or *Rhodosporidium toruloides* strain CBS 349 or *Rhodosporidium toruloides* strain CBS 14 or from a host cell comprising a recombinant DNA molecule having a nucleotide sequence encoding at least a functional part of an Eph, said nucleotide sequence being obtained from above mentioned strains.

The general procedure for cloning, characterization and overexpression of a nucleotide sequence encoding a functional part of an Eph from said basidiomycetous yeast genera in host cells is known to one skilled in the art and can be performed for example according to Visser et al. Appl. Microbiol. Biotechnol., 2000, vol. 53, 415.

The isolation of cDNA molecules encoding at least for a functional part of an Eph of *Rhodotorula glutinis* strain CBS 8761 or *Rhodotorula araucariae* strain CBS 6031 or *Rhodosporidium toruloides* strain CBS 349 or *Rhodosporidium toruloides* strain CBS 14 is described in the examples.

Preferred host cells are bacteria, particularly preferred is *Escherichia coli* (*E. coli*).

The efficient production of Eph in *E. coli* may be enhanced by the co-expression of molecular chaperones and chaperonins according to the description of Gottesman et al., Current Opinion in Microbiology, 2000, vol. 3, p. 197–202.

Another possibility is the lowering of cultivation temperature to decrease the production rate of the recombinant Eph. For example, the specific activity of *E. coli* BL21(DE3) (pEph1) (see examples) increased from 1.5 U per mg of protein at 37° C. to 10 U per mg at 30° C. and 15 U per mg at 21° C.

Moreover an increased cultivation volume of 10 l (versus 450 ml) lead to an specific activity of 23 U per mg of protein at 21° C. other conditions being not changed.

The process for kinetic resolution of epoxides of formula (I) may be carried out at temperatures e.g. ranging from 0 to 50° C., preferably from 10 to 40° C.

The pH for example may range e.g. from 4 to 10, preferably from 5 to 8.

The starting concentration of epoxide is not limited but to achieve higher reaction rates a starting concentration, which exceeds 80% of the solubility of epoxide in the reaction mixture is preferred. This includes the presence of solid epoxide.

The epoxide may also be metered to the reaction mixture continuously.

Solvents which are useful herein may be for example water, mixtures of water with water miscible organic solvents or mixtures of water and water miscible organic solvent mixtures. Two phase systems comprising water and a water inmiscible solvent or solvent mixture like, for example, toluene, dichloromethane, ethylacetate and n-hexane or mixtures thereof are also applicable. The organic solvent or the organic solvent mixtures can be added at maximum in such an amount, that a significant denaturation of the Eph is prevented. Suitable solvents are for example acetone, methanol, ethanol, iso-propanol N,N-dimethyl-form-amide, dimethylsulfoxide and N-methylpyrolidone. Also, a buffer may be added to the reaction mixture.

The amount of microorganisms or crude or pure preparations thereof employed in the reaction is not critical at all.

The progress of reaction may be monitored by standard procedures known to one skilled in the art, which includes for example gas chromatography measurements on chiral columns. In one embodiment of the invention the reaction is stopped when one enantiomer or pair of diastereomers is found to be in excess compared to the other enantiomer or pair of diastereomers.

In a preferred embodiment of the invention the reaction is stopped when one enantiomer of a vicinal diol of the general formula (II) wherein $R^1$ represents a carboxylic group or a derivative thereof, $R^2$ and $R^3$ are identical and represent hydrogen or straight-chain $C_1$–$C_{12}$-alkyl or $R^2R^3C$ as whole represents a carbocycle is found in an enantiomeric excess of at least 90%.

In a more preferred embodiment of the invention the reaction is stopped when one enantiomer of a vicinal diol of the general formula (II) wherein $R^1$ represents a carboxylic group or a derivative thereof $R^2$ and $R^3$ are identical and represent hydrogen or straight-chain $C_1$–$C_{12}$-alkyl or $R^2R^3C$ as whole represents a carbocycle is found in an enantiomeric excess of at least 95%.

The reaction may be stopped for example by the addition of organic solvents in such an amount that denaturation of Eph to a large extent takes place. Moreover the addition of salts as well as heating or the application of microwaves is possible. In these cases where whole cells are used also centrifugation and subsequent separation of the supernatant liquid may be employed.

The workup may be performed for example by selective extraction using two different solvents or two different solvent mixtures or by chromatography. Neutral epoxides or diols may also be separated by distillation.

The enzyme catalysed process for kinetic resolution of functionalized epoxides in the presence of an Eph derived from a microorganism according to the present invention proceeds under very mild reaction conditions and starts from easily available racemic epoxides which is advantageous compared to all chemical procedures known so far.

EXAMPLES

General Methods and Materials:

If not stated otherwise all standard manipulations were carried out according to Sambrook J., Fritsch E. F., Maniatis T., Molecular cloning, A laboratory manual, Cold Spring Harbor Laboratory Press, Cold Spring Harbor, N.Y., 1989.

Nucleotide Sequence Determination:

Nucleotide sequences were determined using AmpliTaq FS DNA polymerase fluorescent dye terminator reactions as recommended by the supplier (Perkin-Elmer)

Reverse Transcription (RT):

RNA, NotI primer adapter (1 µg/µl) and water were mixed (total volume 12 µl), heated and cooled as described in Examples 4, 5 and 6. Subsequently, the following ingredients were added to this mixture: 1 µL dNTP mix (25 mM each), 1 µL Superscript Reverse Transcriptase (GibcoBRL, 200 U/µL), 4 µL 5×first strand buffer (GibcoBRL) and 2 µL dithiotreitol (DTT, 0.1 M). The RT reaction was conducted for 1 hour at 40° C. The reaction was stopped by incubation of the reaction mixture at 90° C. for 5 minutes.

Polymerase Chain Reaction (PCR):

In general the PCR reaction mixture contained the following:

Template: up to 2 µl (RT or PCR reaction mixture or chromosomal DNA)

Forward primer (50 ng/µl): 1 or 2 µl

Reverse primer: (50 ng/µl ): 1 or 2 µl dNTP mixture (2.5 mM each): 4 µl

10×reaction buffer (corresponding to the polymerase used): 5 µl

Polymerase (PWO, Supertaq or Expand High Fidelity): 0.5 to 0.75 µl

Water: to a final volume of 50 µl

Both the amount and type of template, primers and polymerase as well as the PCR cycle settings are described in the corresponding examples.

Strains:

*Escherichia coli* XL1-BlueMRF' (Stratagene, La Jolla, Calif., USA). *Escherichia coli* BL21(DE3) (Novagen Inc., Madison, Wis., USA). *Rhodosporidium toruloides* CBS 349, *Rhodosporidium toruloides* CBS 14, *Rhodotorula araucariae* CBS 6031 and *Rhodotorula glutinis* CBS 8761 (Centraal Bureau voor Schimmelcultures, Utrecht, The Netherlands).

Plasmids:

pKK223-3: prokaryotic expression vector (Amersham Pharmacia Biotech Benelux, Roosendaal, The Netherlands).

pET28a(+): prokaryotic expression vector (Novagen Inc., Madison, Wis., USA).

pUC19: cloning vector (New England Biolabs Inc., Beverly, Mass., USA).

pGEM-T Easy: PCR product cloning vector (Promega Benelux B. V., Leiden, The Netherlands).

Primers:

Nucleotide codes: N: A+T+C+G, W: A+T, S: C+G, I: deoxyinosine, Y: C+T, V: A+C+G, R: A+G, D: A+T+G.

Media:

Luria-Bertani (LB) medium (10 g of tryptone, 5 g of yeast extract and 10 g NaCl per liter water) was used. Two percent (w/v) of agar was added to solidify the medium if necessary. Fifty µg of kanamycin was added per ml of medium to select for *E. coli* harboring pET28a(+) or derivatives thereof. Fifty µg of ampicillin was added per ml of medium to select for *E. coli* harboring pKK223-3, pUC19, pGEM-T Easy or derivatives thereof. SOC medium was used to recover *E. coli* cells after electroporation (see below). SOC medium: 2% (w/v) bacto tryptone, 0.5% (w/v) bacto yeast extract, 10 mM NaCl, 2.5 mM KCl, 10 mM $MgCl_2$, 10 mM $MgSO_4$ and 20 mM glucose.

Glucose containing medium: A mineral medium (Hartmans S., Kaptein A., Tramper J., de Bont J. A. M., Appl. Microbiol. Biotechnol. 37, 1992, 796–801) containing 10 mg EDTA, 2 mg $ZnSO_4.7H_2O$, 1 mg $CaCl_2.2H_2O$, 5 mg $FeSO_4.7H_2O$, 0.2 mg $Na_2MoO_4.2H_2O$, 0.2 mg $CuSO_4.5H_2O$, 0.4 mg $CoCl_2.6H_2O$, 1 mg $MnCl_2.4H_2O$, 2 g $(NH_4)_2SO_4$, 0.1 g $MgCl_2.6H_2O$, 1.55 g $K_2HPO_4$ and 0.85 g NaH$_2$PO$_4$.H$_2$O per liter water was supplemented with 2 g yeast extract and 10 g glucose.

Example 1

Isolation of Total RNA from Yeast Species:

The yeast strain was cultivated at 30° C. in 200 ml glucose containing medium to an OD$_{660}$=1. Cells were harvested by centrifugation (16,300×g, 5 minutes, 4° C.) and washed in cold sterile water. The cell pellet was resuspended in 1 ml of cold sterile water. This cell suspension was transferred to a mortar containing liquid nitrogen. Cells were broken by grinding the frozen cell suspension. The broken cells were transferred to a centrifuge tube containing 5 ml of RNAzol (Cinna/Biotecx Laboratories International inc., Texas, USA) and 0.5 ml chloroform. The tube was closed and vigorously shaken (by hand) for 15 seconds. After incubation on ice for 15 minutes the tube was centrifuged (12,000×g, 4° C. and 15 minutes). The aqueous upper phase (4 ml) was transferred to a clean tube, an equal volume of isopropanol was added and was stored at −20° C. for 16 hours to precipitate the RNA. The tube was centrifuged for 15 minutes at 12,000×g and 4° C. The white pellet, containing the RNA, was washed twice with 1 ml of 70% (V/V) ethanol by vortexing and centrifugation at 7,500×g (40° C. and 8 minutes). Then the pellet was air-dried for 15 minutes and dissolved in 400 µL of diethyl pyrocarbonate (DEPC) treated water and used for further experiments.

Example 2

Chromosomal DNA Isolation from *Rhodotorula araucariae* Strain CBS 6031:

*Rhodotorula araucariae* CBS 6031 was cultivated at 30° C. in 200 ml glucose containing medium to an OD$_{660}$=7. Cells were harvested by centrifugation (16,300×g, 5 minutes, 4° C.) and washed in cold sterile water. The cell pellet was resuspended in 1 ml of cold sterile water. This cell suspension was transferred to a mortar containing liquid nitrogen and 1 gram of alumina type-A5 (Sigma). Cells were broken by grinding the frozen cell suspension. The broken cells were added to a centrifuge tube containing 5 ml of DNA extraction buffer (50 mM Tris, 10 mM MgCl$_2$, 50 mM NaCl, 1% (w/v) SDS, pH 7.4). Chromosomal DNA was isolated from this mixture by repeated phenol/chloroform extractions and an ethanol precipitation step. The co-purified RNA was degraded by incubation with DNase free RNase A (10 µg/ml). A final phenol/chloroform extraction resulted in the purified chromosomal DNA preparation.

Example 3

Transformation of *E. coli* by Electroporation:

*E. coli* was cultivated in LB medium lacking NaCl to an OD$_{600}$ of 0.5. Cells were washed twice in an equal volume of ice cold demineralized water and once in an equal volume of 10% glycerol in demineralized water. After centrifugation (1,000×g, 10 minutes) cells were resuspended in 0.05 volume of 10% glycerol in demineralized water. Hundred µl of cells were mixed with plasmid DNA or ligation mixture and transferred to an electroporation cuvette (0.2 cm). A pulse was given of 2.5 kV, 200Ω and 25 µF. Immediately after the pulse, 1 ml of SOC medium was added. The transformation mixture was transferred to a 1.5 ml Eppendorf tube and incubated at 37° C. for 1 hour. Aliquots were spread onto solid LB agar plates containing the appropriate antibiotic.

Example 4

Isolation of the Epoxide Hydrolase-encoding cDNA Sequence from *Rhodotorula araucariae* Strain CBS 6031:

Alignment of the epoxide hydrolase amino acid sequences from *Xanthophyllomyces dendrorhous*, *Rhodotorula glutinis* CBS8761 and *Aspergillus niger* revealed conserved domains. Based on these conserved regions, two degenerate primers named PSMPGY, corresponding to conserved domain SMPGY, and PANEH4A, corresponding to conserved domain GGHFAALE, were designed. In order to synthesize a *R. araucariae* CBS 6031 epoxide hydrolase specific probe a PCR using primers PSMPGY and PANEH4A was conducted using chromosomal DNA as template. The chromosomal DNA was isolated as described in example 2 and the chromosomal DNA preparation contained 1 µg of chromosomal DNA per µl. The PCR reaction was performed using 0.5 µl chromosomal DNA, 0.5 µl PSMPGY (500 ng), 0.5 µl PANEH4A (500 ng) and 0.5 µl Supertaq polymerase (2.5 U). The PCR conditions were: 8 min at 94° C., followed by 30 cycles of 1 min at 94° C., 1 min at 55° C., 3 min at 72° C. and ending by 5 min at 72° C. The thermal cycler used was a Perkin Elmer 9700. A 1.2 kb PCR product was amplified as was observed by agarose gel electrophoresis. This product was excised from the gel and purified using the QIAEXII kit from Qiagen. The purified product was inserted in the cloning vector PGEM-T Easy. This construct was transferred to *E. coli* XI1-BlueMRF' as described in example 3. This strain was used to amplify the construct, which was subsequently isolated by standard techniques. The nucleotide sequence was translated and visually analyzed. It was concluded that a 1.2 kb fragment, denominated RAEH1, of the putative epoxide hydrolase-encoding gene from *R. araucariae* was cloned as an epoxide hydrolase specific motif was found: GGDWGS. This motif contains the putative nucleophilic residue of the catalytic triad. Specific *R. araucariae* epoxide hydrolase primers, P60315 and P60315N were designed based on the nucleotide sequence of RAEH1. These primers were used to amplify the 5' cDNA end using the 5'/3' RACE kit from Roche according to their instructions. Total RNA was isolated as described above resulting in 600 ng/µl. Primer P60315 was used for the first strand cDNA synthesis in the 5' RACE experiment to obtain the 5'-part of the *R. araucariae* CBS6031 epoxide hydrolase encoding cDNA. The PCR reaction was performed using 5 µl dA-tailed cDNA, 1 µl oligo dT-anchor primer (5'/3' RACE Kit), 1 µl P60315 (50 ng), 1 µl dNTP (5'/3' RACE Kit), 5 µl 10×Expand High Fidelity polymerase reaction buffer (Roche) and 0.75 µl Expand High Fidelity polymerase (2.6 U, Roche). The PCR conditions were: 3 min at 94° C., followed by 10 cycles of 0 min 15 sec at 94° C., 0 min 30 sec at 50° C., 1 min at 72° C., followed by 25 cycles of 0 min 15 sec at 94° C., 0 min 30 sec at 50° C., 1 min at 72° C. with a cycle elongation of 5 sec for each cycle, and ending by 7 min at 72° C. The thermal cycler used was a Perkin Elmer 9700.

This first PCR did not reveal a specific PCR product. Therefore, a second PCR was performed. The 2$^{nd}$ PCR reaction was performed using 1 µl of the 1$^{st}$ PCR reaction mixture, 1 µl oligo dT-anchor primer (5'/3' RACE Kit), 1 µl P60315N (50 ng), 1 µl dNTP (5'/3' RACE Kit), 5 µl 10×Expand High Fidelity polymerase reaction buffer (Roche) and 0.75 µl Expand High Fidelity polymerase (2.6 U, Roche). The PCR conditions were identical to those of the first round of PCR. The reaction mixture contained a specific product of approximately 570 bp as was observed by agarose gel electrophoresis. This product was excised from the gel and purified using the QIAEXII kit from Qiagen. The purified product was used in a ligation reaction to insert it into cloning vector pGEM-T Easy. This ligation mixture was transferred to *E. coli* XL1-BlueMRF' as described in Example 3. This strain was used to amplify the construct, which was subsequently isolated by standard techniques. The nucleotide sequence was determined as described above. The nucleotide sequence was translated and compared to that of the *Rhodotorula Glutinis* CBS 8761 epoxide hydrolase amino acid sequence. It revealed to be similar, but not identical, to the N-terminal amino acid sequence of *Rhodotorula Glutinis* CBS 8761. Furthermore, an epoxide hydrolase specific motif, HGWP corresponding to the putative oxyanion hole of the enzyme, was present. These results indicated that the 5'-part (corresponding to the N-terminal part of the enzyme) of the *Rhodotorula araucariae* CBS 6031 epoxide hydrolase-encoding cDNA was cloned.

Example 5

Isolation of the Epoxide Hydrolase-encoding cDNA Sequence from *Rhodosporidium toruloides* Strain CBS 349:

The epoxide hydrolase-encoding cDNA from *Rhodosporidium toruloides* CBS 349 was isolated by using the PCR technique. First, total RNA was isolated as described in example 1. The total RNA concentration found was 1.3 µg/µl. A reverse transcriptase reaction was performed to synthesize single stranded cDNA molecules. One µl of the total RNA preparation was mixed with 2 µl NotI primer adapter (Stratagene) and 9 µL water in a small scale reaction tube. The mixture was heated at 90° C. for 3 minutes and subsequently put on ice. Additional ingredients were added and the reaction was conducted as described in Example 4.

To amplify the epoxide hydrolase encoding cDNA from *Rhodosporidium toruloides* CBS 349 by means of PCR two primers, derived from the terminal sequences of the *Rhodotorula glutinis* CBS8761 EPH1 cDNA, were used. Primer PEHATG contains the ATG start codon and an EcoRI restriction endonuclease site, while primer PEHTAG contains the TAG stop codon and a PstI restriction endonuclease site. The PCR reaction was performed using 2 µl of the RT reaction mixture, 1 µl PEHATG, 1 µl PEHTAG, 0.5 µL PWO polymerase (2.5 U, Roche). The PCR conditions were: 5 min at 94° C., followed by 30 cycles of 1 min at 94° C., 1 min 30 sec at 50° C., 2 min at 72° C. and ending by 10 min at 72° C. The thermal cycler used was a Perkin Elmer 480. This first round of PCR did not reveal a specific PCR product. Therefore, a second round of PCR was performed. The second round PCR reaction was performed using 2 µl of the 1$^{st}$ round PCR reaction mixture, 2 µl PEHATG, 2 µl PEHTAG, 0.5 µL PWO polymerase (2.5 U). The PCR conditions were: 5 min at 94° C., followed by 30 cycles of 1 min at 94° C., 1 min 30 sec at 50° C., 1 min 40 sec at 72° C. and ending by 10 min at 72° C. The PCR mixture contained a specific product of approximately 1250 bp as was observed by means of agarose gel electrophoresis. This product was excised from the gel and purified using the QIAEXII kit from Qiagen. Both the purified product and cloning vector pUC19 were digested with restriction endonucleases EcoRI and PstI. These digested DNA fragments were used in a standard ligation reaction. This ligation mixture was transferred to *E. coli* XL1-BlueMRF' as described in Example 3 above. This strain was used to amplify the construct, which was subsequently isolated by standard techniques. The nucleotide sequence of the inserted cDNA sequence was determined as described in the general methods and materials section. The nucleotide sequence was analyzed by the DNA-STAR software package. Translation of the nucleotide sequence of the cloned PCR product and subsequent amino acid comparison to known epoxide hydrolase amino acid sequences revealed that the cloned cDNA encoded an epoxide hydrolase. Moreover, the nucleotide sequence was found to be identical to the nucleotide sequence of the *Rhodotorula glutinis* CBS8761 epoxide hydrolase-encoding cDNA.

Example 6

Isolation of the Epoxide Hydrolase-encoding cDNA Sequence from *Rhodosporidium toruloides* Strain CBS 14:

The epoxide hydrolase encoding cDNA from *Rhodosporidium toruloides* CBS 14 was isolated by PCR techniques. First, total RNA was isolated as described above in the methods and materials section. The total RNA concentration found was 5.8 µg/µL. A reverse transcriptase reaction was performed to synthesize single stranded cDNA. Half a µL of the total RNA preparation was mixed with 2 µL NotI primer adapter (Stratagene) and 9.5 µL water. Additional ingredients were added and the reaction was conducted as described above.

To amplify the epoxide hydrolase encoding cDNA of *Rhodosporidium toruloides* CBS 14 by means of PCR two primers, derived from the terminal sequences of the *Rhodotorula glutinis* CBS8761 EPH1 cDNA, were used. Primer PEHATG contains the ATG start codon and an EcoRI restriction endonuclease site, while primer PEHTAG contains the TAG stop codon and a PstI restriction endonuclease site. The PCR reaction was performed using 2 µl of the RT reaction mixture, 2 µl PEHATG, 2 µl PEHTAG, 0.5 µL Supertaq polymerase (2.5 U, SphearoQ, Leiden, The Netherlands). The PCR conditions were: 5 min at 94° C., followed by 30 cycles of 0 min 30 sec at 94° C., 1 min at 50° C., 1 min 40 sec at 72° C. and ending by 5 min at 72° C. The thermal cycler used was a Perkin Elmer 9700. The PCR reaction mixture contained a specific product of approximately 1250 bp as was observed by means of agarose gel electrophoresis. This product was excised from the gel and purified using the QIAEXII kit from Qiagen. A ligation reaction was performed to insert the purified product into cloning vector pGEM-T Easy. This ligation mixture was transferred to *E. coli* XL1-BlueMRF' as described in Example 3. This strain was used to amplify the construct, which was subsequently isolated by standard techniques. The nucleotide sequence of the inserted cDNA insert was determined as described in the general methods and materials section. The nucleotide sequence was analyzed by the DNA-STAR software package. Translation of the nucleotide sequence of the cloned PCR product and subsequent amino acid comparison to known epoxide hydrolase amino acid sequences revealed that the cloned cDNA encoded an epoxide hydrolase. Moreover, the nucleotide sequence was very similar to that of *Rhodotorula glutinis* CBS8761 and *Rhodosporidium toruloides* CBS 349 but not identical.

Example 7

Construction of *E. coli* BL21(DE3)[pEph1]:

Plasmid pKKRgEph1 is a pKK223-3 derivative, which contains the epoxide hydrolase-encoding cDNA from *Rhodotorula glutinis* (Visser H., Vreugdenhil S., de Bont J.

A. M., Verdoes J. C., Appl. Microbiol. Biotechnol. 53, 2000, 415–419). The *Rhodotorula glutinis* Eph1 encoding DNA sequence was released from plasmid pKKRgEph1 as a 1230 bp DNA fragment by cutting the plasmid with restriction endonucleases EcoRI and HindIII. Plasmid pET28a(+) (FIG. 4) was also treated with the same restriction endonucleases. Both reactions were analyzed afterwards on a 1% (w/v) agarose gel. The 1230 bp EPH1 DNA fragment and the linearized pET28a(+) DNA fragment were excised from the gel and purified using the Qiaex II kit (Qiagen) according to the instructions specified by the manufacturer. A ligation mixture was prepared containing 3 µl of the purified 1230 bp EPH1 fragment, 1 µl of the purified linearized pET28a(+) plasmid, 2 µl of 5 times concentrated T4-DNA-ligation buffer, 1 µl (1 Weiss unit) T4-DNA-ligase (GibcoBRL) and 3 µl of water. This mixture was incubated at 14° C. for 16 hours. Two µl of the ligation mixture were mixed with 100 µl competent *E. coli* XL1-blueMRF' cells, electroporation was carried out as described in Example 3 above. After plating the cell/DNA mixture on agar plates and an incubation at 37° C. for 16 hours 8 colonies were picked from the ampicillin (50 µg/ml) containing LB-agar plates. Plasmid DNA was isolated from these colonies by a standard alkaline lysis protocol (Sambrook J., Fritsch E. F., Maniatis T., Molecular Cloning, A Laboratory Manualanual, Cold Spring Harbor Laboratory Press, Cold Spring Harbor, N.Y., 1989) and treated with EcoRI and HindIII. Agarose gel electrophoresis using a 1% (w/v) agarose gel of these samples indicated that, in all 8 cases, the 1230 bp EPH1 fragment indeed was inserted in plasmid pET28a(+). The resulting plasmid was denominated pEph1. One µl of one of the 8 pEph1 solutions was mixed with 100 µl *E. coli* BL21(DE3) cells, which were prepared for transformation by electroporation as described in Example 3. After electroporation as described in Example 3 one colony was picked from a kanamycin (50 µg/ml) containing LB-agar plate. Plasmid DNA was isolated and treated with EcoRI and HindIII. Agarose gel electrophoresis using a 1% (w/v) agarose gel of this samples indicated that the plasmid was plasmid pEph1. Therefore, the corresponding *E. coli* BL21(DE3) strain contains pEph1 and it was denominated *E. coli* BL21(DE3) [pEph1].

Example 8

Preparation of an *E. coli* BL21(DE3)[pEph1] Pre-culture:

A single *E. coli* BL21(DE3)[pEph1] colony was taken from a LB agar plate, which was supplemented with kanamycin, and used to inoculate 50 ml of kanamycin containing LB medium in a 250 ml Erlenmeyer flask. This culture was incubated at 37° C. and 200 revolutions per minute (rpm) using an innova 4000 incubator shaker (New Brunswick Scientific, The Netherlands) until the optical density at 600 nm ($OD_{600}$) reached 0.5–1. The pre-culture was stored at 4° C. until use.

Example 9

Expression of EPH1:

Two ml of the *E. coli* BL21(DE3)[pEph1] pre-culture (see example 2) were used to inoculate 50-mL of kanamycin containing LB medium in a 250 ml Erlenmeyer flask. This culture was incubated at 21° C. and 200 rpm until $OD_{600}$ reached 0.5–1. Then, EPH1 gene expression was induced by adding 100 µM isopropyl-β-D-thiogalactopyranoside (IPTG) (Diagnostic Chemicals Limited, UK). After 3 hours of incubation the cells were harvested by centrifugation at 4° C. and 20,000×g for 5 minutes and washed with 50 mM potassium phosphate (KPi) buffer (pH 7). The cells were subsequently resuspended in 5 ml KPi-buffer.

Example 10

Small Scale Production of *E. coli* BL21(DE3)[pEph1]:

A 50 ml pre-culture of *E. coli* BL21(DE3)[pEph1] was prepared as described above. Two ml of the *E. coli* BL21 (DE3)[pEph1] pre-culture were used to inoculate 50 ml of kanamycin (50 µl/ml) containing LB medium in a 250 ml Erlenmeyer flask sealed with a air-permeable cotton-wool plug to permit aeration. This culture was incubated at 21° C. and 200 rpm until $OD_{600}$ reached 0.5–1. Five µl of a 1 M isopropyl-β-D-thiogalactopyranoside (IPTG) solution (Diagnostic Chemicals Limited, UK) was added to induce EPH1 gene expression. After 3 hours of incubation the cells were harvested by centrifugation at 4° C. and 20,000×g for 5 minutes. The supernatant was discarded the cell pellet was resuspended in 30 ml of 50 mM potassium phosphate (KPi) buffer (pH 7). The centrifugation step was repeated and the cell pellet was subsequently resuspended in 5 ml KPi-buffer and stored at –20° C.

Example 11

Upscaling of *E. coli* BL21(DE3)[pEph1] Production:

Twenty ml of an *E. coli* BL21(DE3)[pEph1] pre-culture (see example 2) was used to inoculate 500 ml of LB medium, supplemented with 50 µg/mL kanamycin, in a 1 liter Erlenmeyer flask. This culture was incubated for 16 hours at 200 rpm and 37° C. and used to inoculate a 15 liters fermenter (Applikon, Schiedam, The Netherlands). The fermenter was filled with 10 liters of LB medium supplemented with 50 µg/ml kanamycin and pre-cooled to 21° C. The $OD_{600}$ after inoculation was 0.2. During fermentation the fermenter content was agitated by two impellers (250 rpm), cooled (21° C.) and aerated (750 ml air/min). At an $OD_{600}$ of 0.65, which was after 4 hours of incubation, IPTG was added to a final concentration of 100 µM to induce EPH1 gene expression. In the first 5 hours of incubation the pH decreased slowly from 7.16 to 6.72. In the next 19 hours the pH increased slowly to 7.66. After 20 hours of induction the $OD_{600}$ had reached the value of 5. Nine liters of the fermenter culture were withdrawn and the cells were harvested by centrifugation at 10,000×g for 5 minutes and 4° C. The cells were washed with approximately 1 liter of 50 mM KPi-buffer (4° C.) and the centrifugation step was repeated. Finally, the cells were resuspended in a minimal volume of 50 mM KPi-buffer, which resulted in a concentrated cell suspension of 400 ml. This cell suspension was stored in 45 ml aliquots at –20° C.

Example 12

Preparation of Crude Eph1 Enzyme:

Cell extracts (from cell suspensions prepared according to examples 9, 10 and 11) were prepared by sonication (5 minutes, duty cycle 30%, output control 3) using a Branson sonifier 250. To separate the cell extracts in a soluble and an insoluble fraction the disrupted cells in KPi-buffer were centrifuged for 10 minutes at 4° C. and 20,000×g. The supernatant, containing the soluble proteins, was called the S-fraction. The pellet, containing the insoluble proteins and cell debris, was resuspended in an equal volume of KPi-buffer and referred to as the P-fraction.

Example 13

Eph1 Assay:

Crude Eph1 enzyme samples (prepared according to example 12) or whole *E. coli* BL21(DE3)[pEph1] cells (from examples 9, 10 and 11) were diluted in KPi-buffer. One ml of such an diluted enzyme extract was transferred to a small glass reaction tube. The tube was sealed with a rubber plug. The tube was incubated at 35° C. for 3 minutes to equilibrate. A calibrated syringe (SGE) was used to add 1.2 µl 1,2-epoxyhexane, the final concentration of 1,2-epoxyhexane was 10 mM, through the rubber plug into the enzyme solution. The solution (1 ml, total reaction volume) was mixed and immediately a 100 µL headspace sample was taken and analyzed using GC analysis on a Chrompack CP9000 gaschromatograph equipped with a β-cyclodextrin 120 chiral column (Supelco, Zwijndrecht, Netherlands). The temperature settings of the GC were: injector 220° C., oven 47° C. and detector 250° C. Subsequently, headspace samples were taken over a period of 15 minutes with time intervals of 1.5 minutes to follow the kinetic resolution of 1,2-epoxyhexane. The decrease in 1,2-epoxyhexane concentration was plotted against the reaction time. The slope at the beginning of the curve represents the initial reaction speed. The protein content was determined using the Bio-Rad DC Protein Assay (Bio-Rad Laboratories BV, Veenendaal, Netherlands). Specific enzyme activities are expressed as units per mg of protein: U (mg protein)$^{-1}$ or as units per mg of dry cell mass (dry weight, DW): U (mg DW)$^{-1}$. One unit (U) is equivalent to 1 µmol of epoxide converted per minute.

Example 14

Hydrolysis of 1-oxa-spiro[2.5]octane-2-carbonitrile by Whole Cells of *Rhodotorula glutinis*:

The racemic resolution of the epoxy nitriles was performed with 24 g/L (dry weight) of whole resting cells of *Rhodotorula glutinis* CBS 8761 in an aqueous solution of 50 mM potassium phosphate buffer at pH 7.5, 35–37° C. The starting epoxide concentration used was 10 mM. After 150 minutes the resolution was stopped by centrifugation and separation of the supernatant liquid and enantiopure epoxide (>99% ee, GC-analysis) could be obtained with 50% conversion (100% of the theoretical yield).

Example 15

Hydrolysis of 1-oxa-spiro[2.5]octane-2-carbonitrile by Whole Cells of Recombinant *E. coli:*

The racemic resolution of the epoxy nitrile was performed with 2.75 g/L (dry weight) of whole resting cells of *E. coli* BL21(DE3)[pEph1] in an aqueous solution of 50 mM potassium phosphate buffer at pH 7.5, 35– 37° C. The starting epoxide concentration used was 10 mM. After 150 minutes the resolution was stopped by short and rapid heating to 80° C. and enantiopure epoxide (>99% ee, GC-analysis) could be obtained with 50% conversion (100% of the theoretical yield).

Example 16

Hydrolysis of 1-oxa-spiro[2.5]octane-2-carbonitrile by a Cell Free Extract of Recombinant *E. coli:*

The racemic resolution of the epoxy nitrile was performed with the cell free extracts of *E. coli* BL21(DE3)[pEph1] containing 48 mg protein/L in an aqueous solution of 50 mM potassium phosphate buffer at pH 7.5, 35–37° C. The starting epoxide concentration used was 10 mM. After 150 minutes the resolution was stopped by short and rapid heating to 80° C. and enantiopure epoxide (>99% ee, GC-analysis) could be obtained with 50% conversion (100% of the theoretical yield).

Example 17

Isolation of Epoxide and Diol by Selective Extraction:

Two consecutive extraction steps of reaction mixtures obtained according to example 8 with 100 ml isohexane and 100 ml ethyl acetate were carried out. The yield of the epoxide extraction in isohexane was as high as 69%, leading to an overall yield of 34.5%. The diol could be isolated by the subsequent extraction with ethyl acetate with a yield of 73%, which is equal to an overall yield of 36.5%.

Analytical Data for Examples 14–16:

Determination of reaction and extraction progress as well as enantiomeric excess were performed by gas chromatography (GC) using fused silica cyclodextrin capillary column (FS-CYCLODEX alpha-I/P 50 m length, 0.32 mm ID, Chromatography Service GmbH) on an Hewlett-Packard 6890 gas chromatograph equipped with FID detector and using $H_2$ as carrier gas at 120° C. and 0.6 bar pressure.

| Retention times: | |
|---|---|
| Hydroxy-(1-hydroxy-cyclohexyl)-acetonitrile | 12.8 min |
| 1-Oxa-spiro[2.5]octane-2-carbonitrile (enantiomer 1) | 26.5 min |
| 1-Oxa-spiro[2.5]octane-2-carbonitrile (enantiomer 2) | 27.1 min |

NMR-spectroscopy (Bruker 500 MHz)

1-Oxa-spiro[2.5]octane-2-carbonitrile:

$^1$H NMR (CDCl$_3$) $\Delta_H$=1.56–1.99 (10H, m), 3.23 (1H, s, —CH—)

Hydroxy-(1-hydroxy-cyclohexyl)-acetonitrile:

$^1$H NMR (CDCl$_3$): $\Delta_H$=1.23–1.79 (10H, m), 1.83–2.78 (1H, br, —OH), 3.05–3.20 (1H, br, —OH), 4.25 (1H, s, —CH—).

$^{13}$C NMR (CDCl$_3$): $\Delta_C$=21.2 (CH$_2$), 21.3 (CH$_2$), 25.1 (CH$_2$), 32.7 (CH$_2$), 33.5 (CH$_2$), 69.5 (—CH), 73.0 (C$_{quart.}$), 118.5 (—CN)

Examples 18 and 19

Hydrolysis of 2-cyano-3,3-dimethyl-oxirane

Examples 12 and 13 were carried out analogously to examples 8 and 10 using 2-cyano-3,3-dimethyl-oxirane as substrate. The results are shown in Table 1.

TABLE 1

| Epoxide | activity [U/g (dry weight)] whole cell *R. glutinis* | activity [U/g (protein)] cell free extract *E. coli* |
|---|---|---|
| cyclohexane spiro-epoxide-CN | 6 (example 14) | 3000 (example 16) |
| 2-cyano-3,3-dimethyl-oxirane | 3 (example 18) | 300 (example 19) |

The invention claimed is:

1. A process for the stereoselective preparation of an 2,3-dihydroxy carboxylic acid and a derivative thereof, comprising
hydrolyzing a 2,3-epoxycarboxylic acid or a derivative thereof in the in the presence of a polypeptide having epoxide hydrolase activity,
wherein the 2,3-epoxycarboxylic acid or derivative has a formula (I)

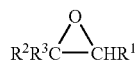
(I)

wherein independently of each other
$R^1$ represents a cyano substituent and
$R^2$ represents hydrogen, straight-chain or branched, cyclic or acyclic $C_1$–$C_{12}$-alkyl, unsubstituted or substituted aryl and
$R^3$ represents hydrogen, straight-chain $C_1$–$C_{12}$-alkyl, or $R^2R^3C$ represents a carbocycle or a heterocycle.

2. The process according to claim 1, wherein the process further comprises converting the 2,3-epoxycarboxylic acid or the 2,3-epoxycarboxylic acid derivative
to vicinal diols of the general formula (II)

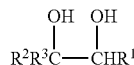
(II)

wherein independently of each other
$R^1$ represents a cyano substituent and
$R^2$ represents hydrogen, straight-chain or branched, cyclic or acyclic $C_1$–$C_{12}$-alkyl, unsubstituted or substituted aryl and
$R^3$ represents hydrogen, straight-chain $C_1$–$C_{12}$-alkyl, or $R^2R^3C$ represents a carbocycle or a heterocycle
in the presence of a polypeptide having epoxide hydrolase activity and which is derived from a microorganism.

3. The process according to claim 2 wherein the conversion is stopped when epoxides of the general formula (I) wherein independently of each other
$R^1$ represents a cyano substituent and
$R^2$ and $R^3$ are identical and represent hydrogen, straight-chain $C_1$–$C_{12}$-alkyl or
$R^2R^3C$ as whole represents a carbocycle
are converted to the correspoding vicinal diols of formula (II) wherein $R^1$, $R^2$ and $R^3$ have the same meaning as mentioned above to such an extent that said vicinal diols have an enantiomeric excess of at least 90%.

4. The process according to claim 2 wherein the conversion is stopped when epoxides of the general formula (I) wherein independently of each other
$R^1$ represents a cyano substituent and
$R^2$ and $R^3$ are identical and represent hydrogen, straight-chain $C_1$–$C_{12}$-alkyl or
$R^2R^3C$ as whole represents a carbocycle
are converted to the corresponding vicinal diols of formula (II) wherein $R^1$, $R^2$ and $R^3$ have the same meaning as mentioned above to such an extent that said vicinal diols have an enantiomeric excess of at least 95%.

5. The process according to claim 1 wherein the polypeptide having epoxide hydrolase activity is derived from a microorganism belonging to the basidiomycetous yeast genera *Rhodotorula*, *Rhodosporidium* or *Trichosporon*.

6. The process according to claim 5 wherein the polypeptide having epoxide hydrolase activity is derived from a microorganism belonging to the basidiomycetous yeast genera *Rhodotorula* or *Rhodosporidium*.

7. The process according to claim 6 wherein the polypeptide having epoxide hydrolase activity is derived from *Rhodotorula glutinis*, *Rhodosporidium toruloides* or *Rhodosporidium toruloides*.

8. The process according to claim 7 wherein the polypeptide having epoxide hydrolase activity is derived from *Rhodotorula glutinis* strain CBS 8761, *Rhodotorula glutinis* strain CBS 6031, *Rhodosporidium toruloides* strain CBS 349 or *Rhodosporidium toruloides* strain CBS 14.

9. The process according to claim 1 wherein the polypeptide having epoxide hydrolase activity is derived from a host cell, comprising a recombinant DNA molecule which comprises a nucleotide sequence encoding at least a functional part of a polypeptide having epoxide hydrolase activity.

10. The process according to claim 9, characterized in that a nucleotide sequence encoding at least a functional part of a polypeptide having epoxide hydrolase activity is derived from a microorganism belonging to the basidiomycetous yeast genera *Rhodotorula* and *Rhodosporidium*.

11. The process according to claim 9, characterized in that a nucleotide sequence encoding at least a functional part of a polypeptide having epoxide hydrolase activity is derived from *Rhodotorula glutinis*, *Rhodosporidium toruloides* or *Rhodosporidium toruloides*.

12. The process according to claim 9, characterized in that a nucleotide sequence encoding at least a functional part of a polypeptide having epoxide hydrolase activity is derived from *Rhodotorula glutinis* strain CBS 8761, *Rhodotorula glutinis* strain CBS 6031, *Rhodosporidium toruloides* strain CBS 349 or *Rhodosporidium toruloides* strain CBS 14.

13. The process according to claim 9 wherein the host cell is a bacterium.

14. The process according to claim 9 wherein the host cell is *E. coli*.

15. The process according to claim 9 wherein the host cell additionally comprises a recombinant DNA molecule which comprises a nucleotide sequence encoding for at least one recombinant chaperone or chaperonine.

16. The process according to claim 1 wherein the temperature is in the range of 0 to 50° C.

17. The process according to claim 1 wherein the pH value is in the range of 4 to 10.

18. The process according to claim 2 wherein the starting concentration of the epoxide according to general formula (I) is at least 80% of the solubility of said epoxide in the reaction media.

19. The process according to claim 1 further comprising providing a water miscible organic solvent or a water miscible organic solvent mixture in an effective amount at maximum, to prevent significant degeneration of polypeptide having epoxide hydrolase.

20. The process according to claim 1 wherein the resulting crude reaction mixture is worked up by selective extraction with two different solvents or two different solvent mixtures.

21. A process for preparing 2,3-dihydroxycarboxylic acids and derivatives thereof comprising hydrolyzing 2,3-epoxycarboxylic acids or derivatives thereof in the presence of a microorganism belonging to the basidiomycetous yeast genera *Rhodotorula, Rhodosporidium* and *Trichosporon*.

* * * * *